United States Patent [19]

Ding et al.

[11] Patent Number: 5,338,729
[45] Date of Patent: Aug. 16, 1994

[54] ANTIBIOTIC 42D005 α AND β

[75] Inventors: Weidong Ding, Nanuet; George A. Ellestad, Pearl River; Darren Abbanat, Cornwall; Valerie Bernan, New City, all of N.Y.

[73] Assignee: American Cyanamid Company, Wayne, N.J.

[21] Appl. No.: 52,724

[22] Filed: Apr. 26, 1993

[51] Int. Cl.$^5$ .................. C07H 17/00; A61K 31/70; A61K 31/71; A61K 31/735
[52] U.S. Cl. ........................... 514/27; 536/16.8; 536/17.3; 536/17.4; 536/18.1
[58] Field of Search ............ 536/16.8, 17.3, 17.4, 536/18.1; 514/27

[56] References Cited

U.S. PATENT DOCUMENTS 5,082,933  1/1992  Schroeder et al. .............. 536/16.8

OTHER PUBLICATIONS

American Type Culture Collection, Catalogue of Bacteria and Phages, (1989), Gherna, R. and Pienta, P. (Editors), 17th Ed., p. 111.
Keller-Scheierlein et al., Helv. Chim. Acta., 1969, 52:127–142.
Kobinata, K. et al., J. Antibiotics, 1980, 33:244-246-1189.
Tomita, F. et al., J. Antibiotics, 1980, 33:940–946.
Waitz, J. A. et al., J. Antibiotics, 1981, 34:1101.

Primary Examiner—Douglas W. Robinson
Assistant Examiner—Francisco C. Prats
Attorney, Agent, or Firm—Kenneth J. Dow

[57] ABSTRACT

This invention relates to antibiotic 42D005α and 42D005β derived from the microorganism Kitasatosporia, which is useful as an antibacterial agent.

12 Claims, 8 Drawing Sheets

ANTIBIOTIC 42D005 α AND β

BACKGROUND OF THE INVENTION

1. Field of the Invention

The invention relates to new antibiotics designated 42D005 α and β, to their production by fermentation, to methods for their recovery and concentration from crude solutions and to processes for their purification. The present invention includes within its scope the agents in dilute form, as crude concentrates, as a complex of all components, in pure form as individual components and a novel strain of Kitasatosporia.

The present invention also relates to the use of the compounds according to the invention in anti-septic or antimicrobial compositions such as disinfectants or preservatives.

2. Description of the Prior Art

Other related antibiotics are described in the literature. Chlorothricin is reported by Keller-Schierlein, W. et al., Helv. Chim. Acta, 52, 127–142(1969). Antlermicin A is described by Kobinata, K. et al., J. Antibiotics, 33, 244–246(1980). Tetrocarcin is reported by Tomita, F. et al., 33, 668, 940, 946(1980). Kijanimicin is described by Waitz, J. A. et al., J. Antibiotics, 34, 1101(1981). Antibiotic BMY-42448 is reported in U.S. Pat. No. 5,082,933 issued Jan. 21, 1992.

DESCRIPTION OF THE PREFERRED EMBODIMENTS

The structure of the new antibiotic 42D005α is:

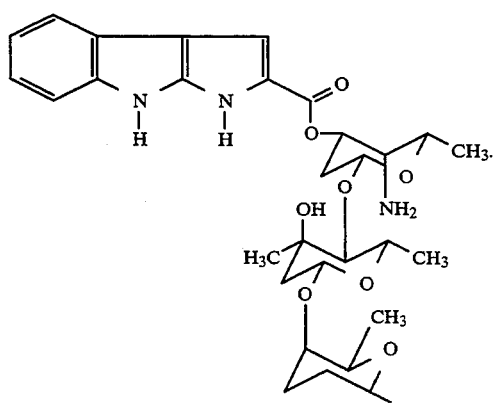

-continued

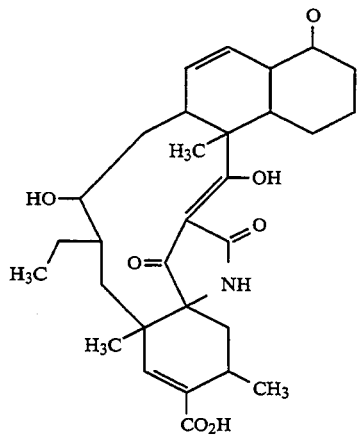

The physico-chemical characteristics of 42D005α are as follows:

2D005α

Figure 1:
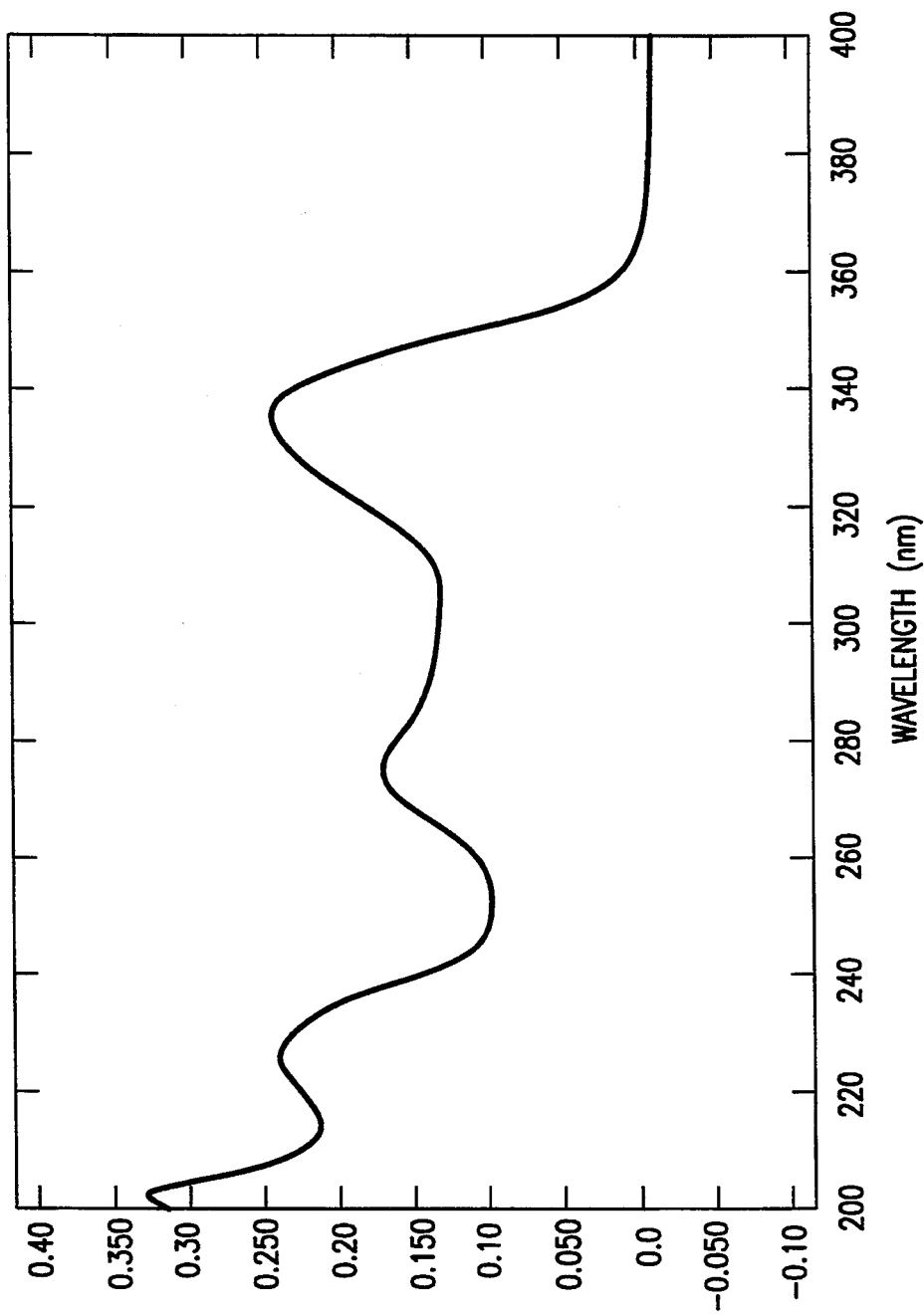
FIG. 1 shows an ultraviolet absorption spectrum of 42D005α.

1. Molecular weight: 1096;

cal: 1119.5513 (M+Na+) high resolution mass spectrum;

2. Apparent molecular formula: $C_{60}H_{80}N_4O_{15}$;

3. Specific rotation: $[\alpha]_D^{25} = -30+8$ (0.1% DMSO);

4. Ultraviolet absorption spectrum: as shown in FIG. 1

10 μg/ml in methanol

Figure 2:
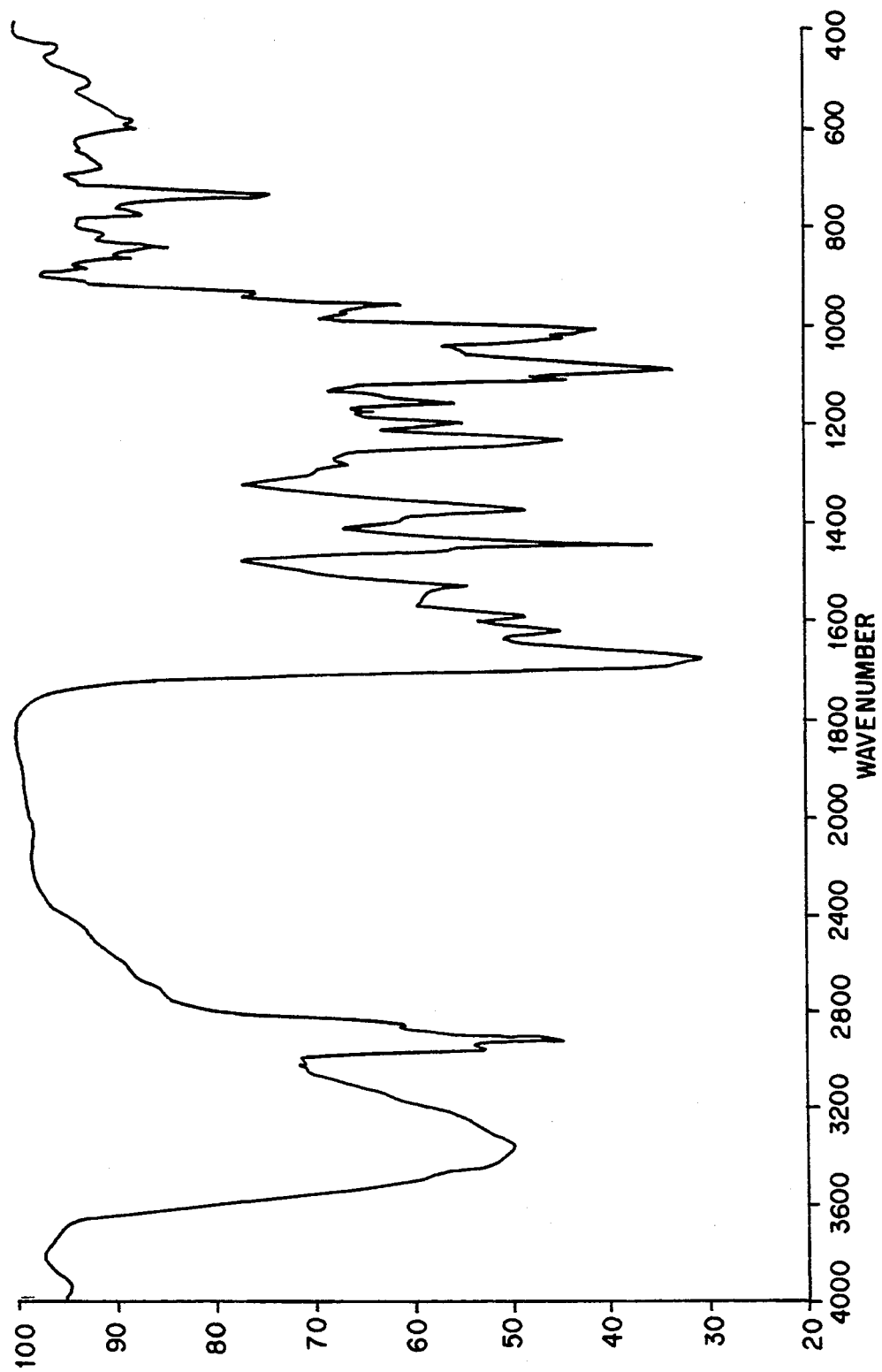
FIG. 2 shows an infrared absorption spectrum of 42D005α.

226nm (ξ,26,100), 273nm (ξ,18,500), 335nm (ξ,26,200);

5. Infrared absorption spectrum: as shown in FIG. 2 ($cm^{-1}$)

3380, 3063, 2971, 2878, 1682, 1627, 1598, 1539, 1447, 1382, 1293, 1239, 1206, 1164, 1114, 1091, 1032, 1017, 987, 972, 745.

Figure 3:
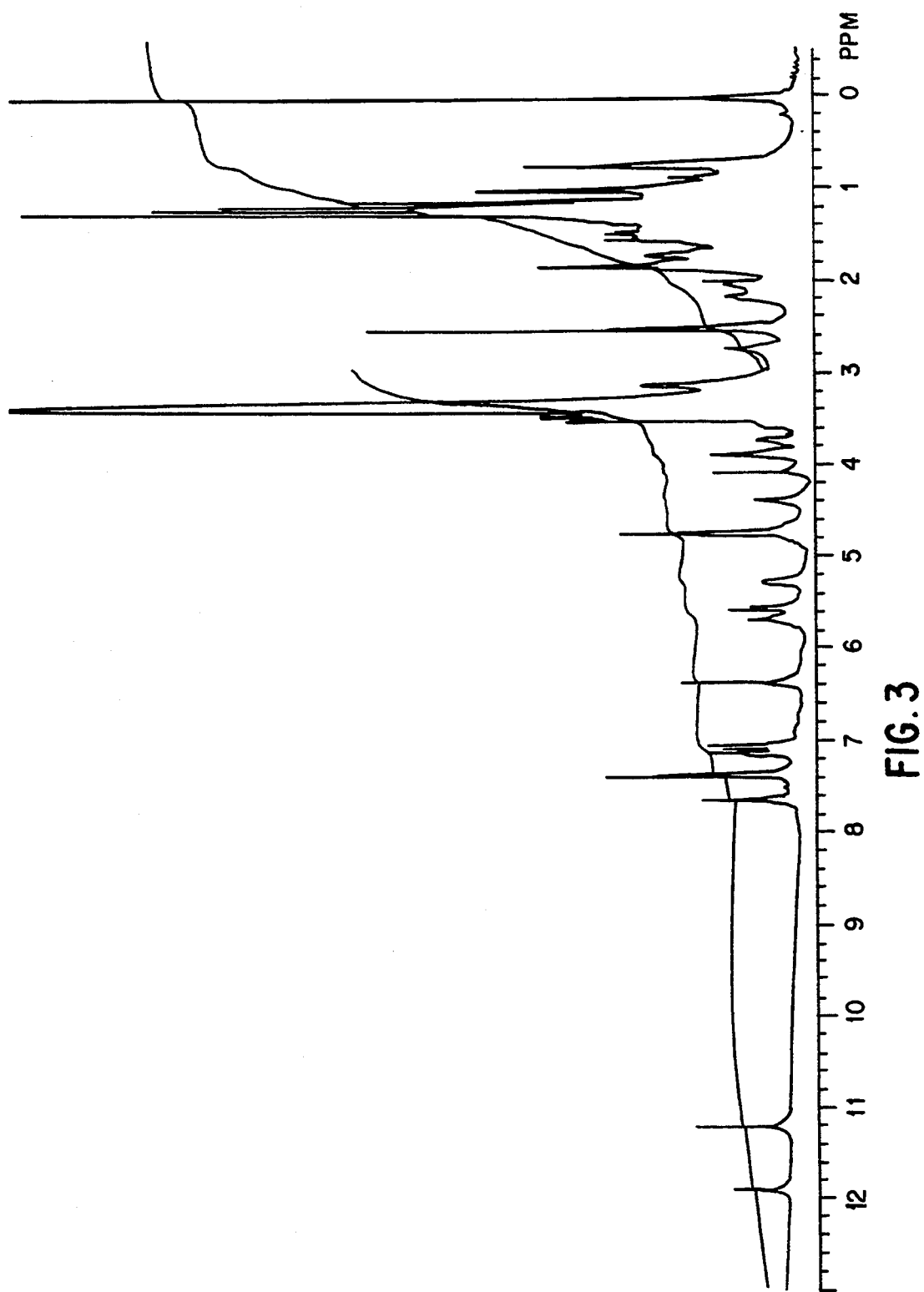
FIG. 3 shows a proton magnetic resonance spectrum of 42D005α.
Figure 4:
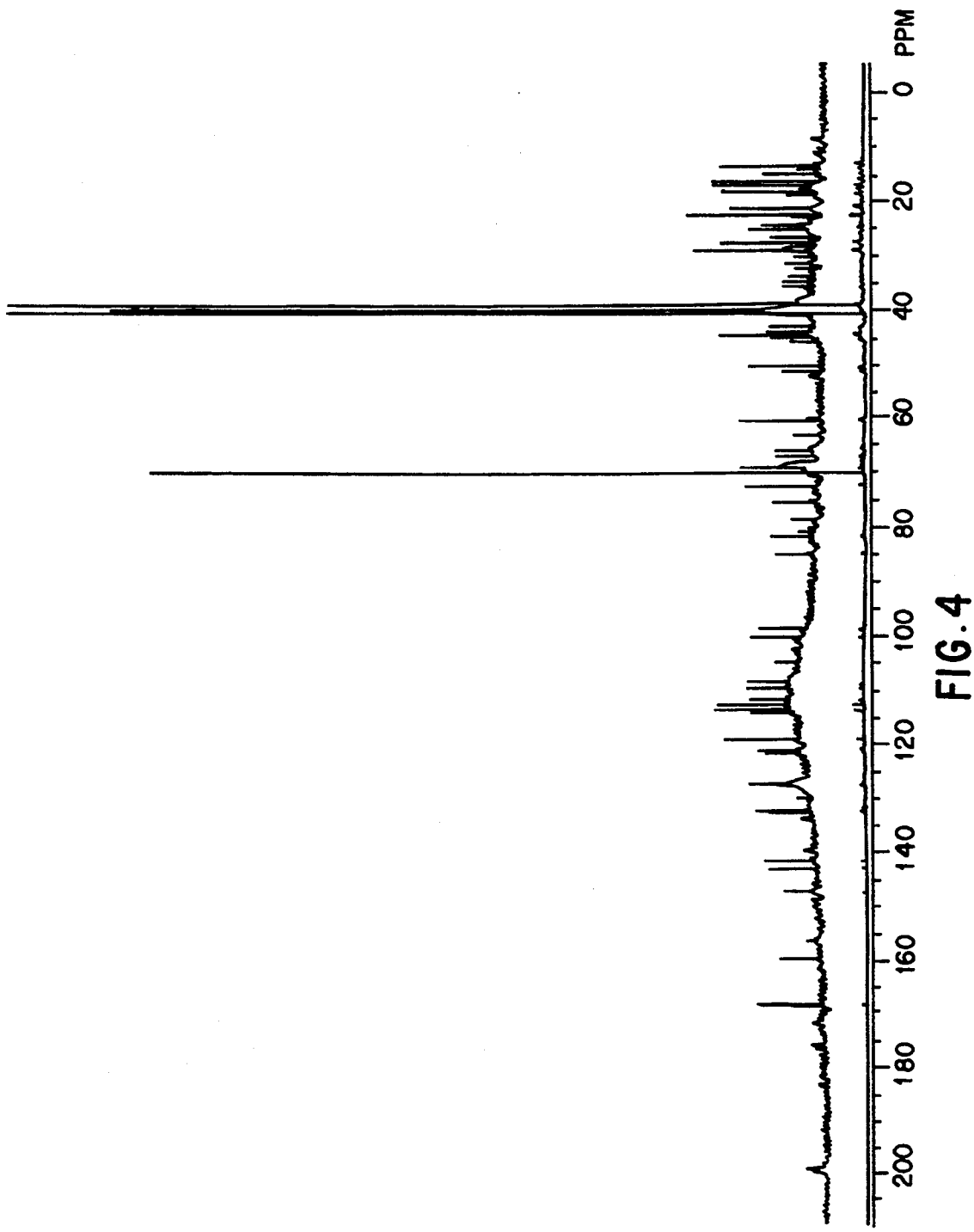
FIG. 4 shows a carbon-13 nuclear magnetic resonance spectrum of 42D005α.

6. Proton nuclear magnetic resonance spectrum: as shown in FIG. 3:

7. Carbon-13 nuclear magnetic resonance spectrum: as shown in FIG. 4;

The structure of the new antibiotic 42D005β is:

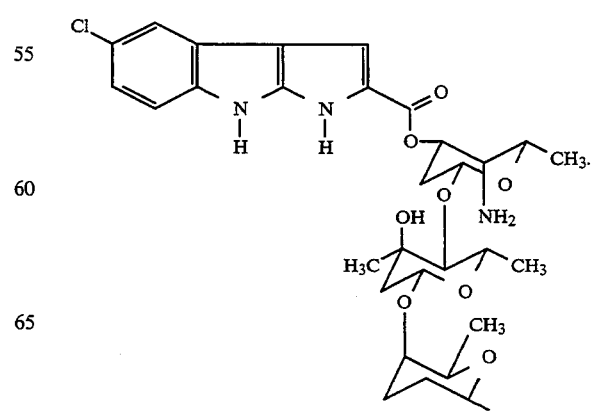

-continued

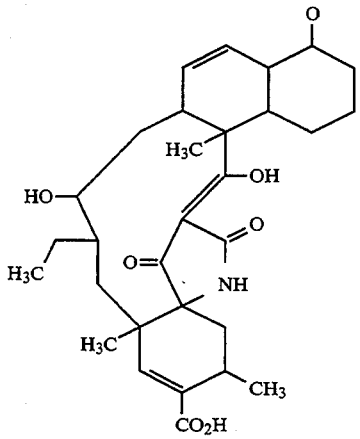

The physico-chemical characteristics of 42D005β are as follows:

2D005β

Figure 5:
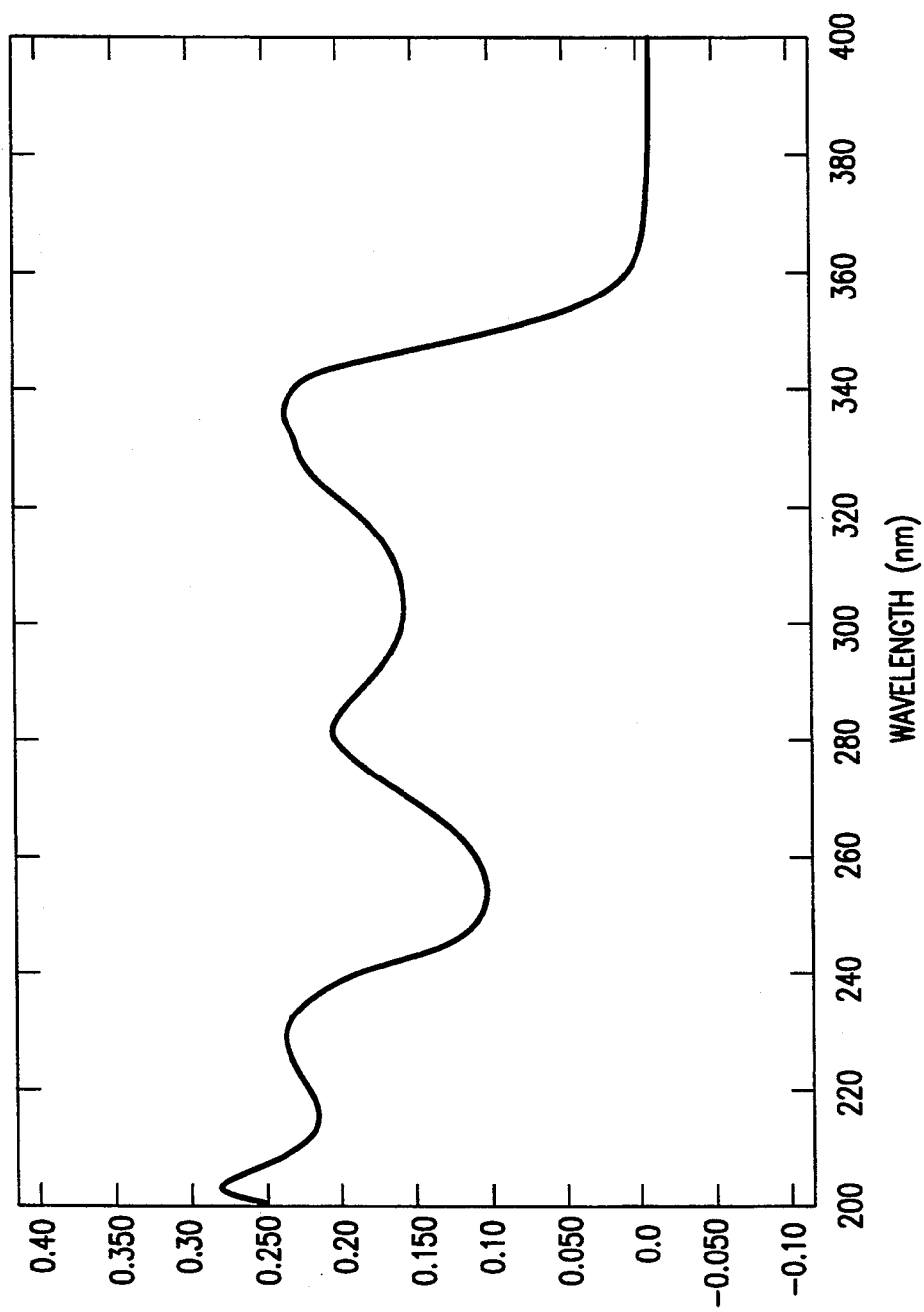
FIG. 5 shows an ultraviolet absorption spectrum of 42D005β.
Figure 6:
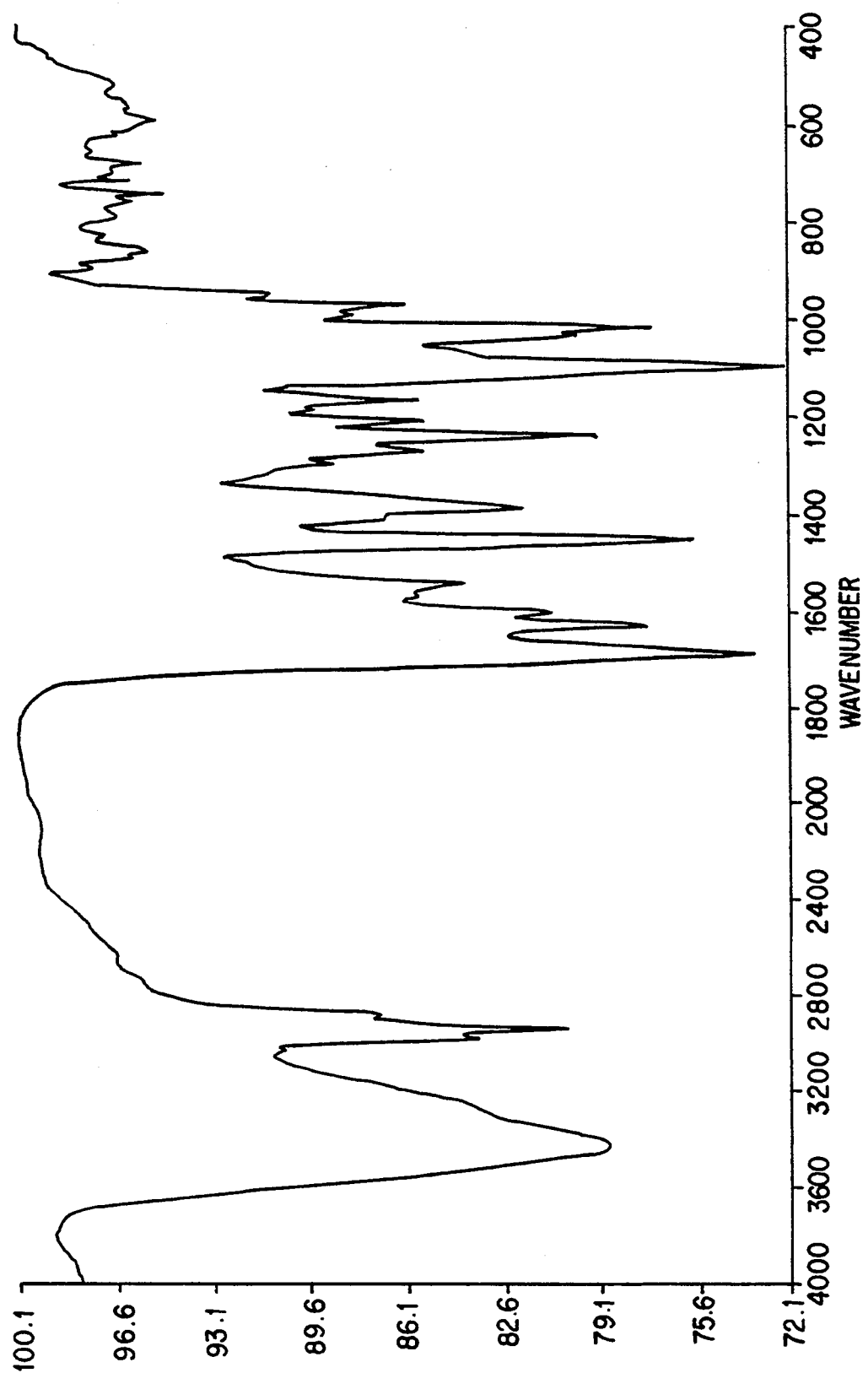
FIG. 6 shows an infrared absorption spectrum of 42D005β.
Figure 7:
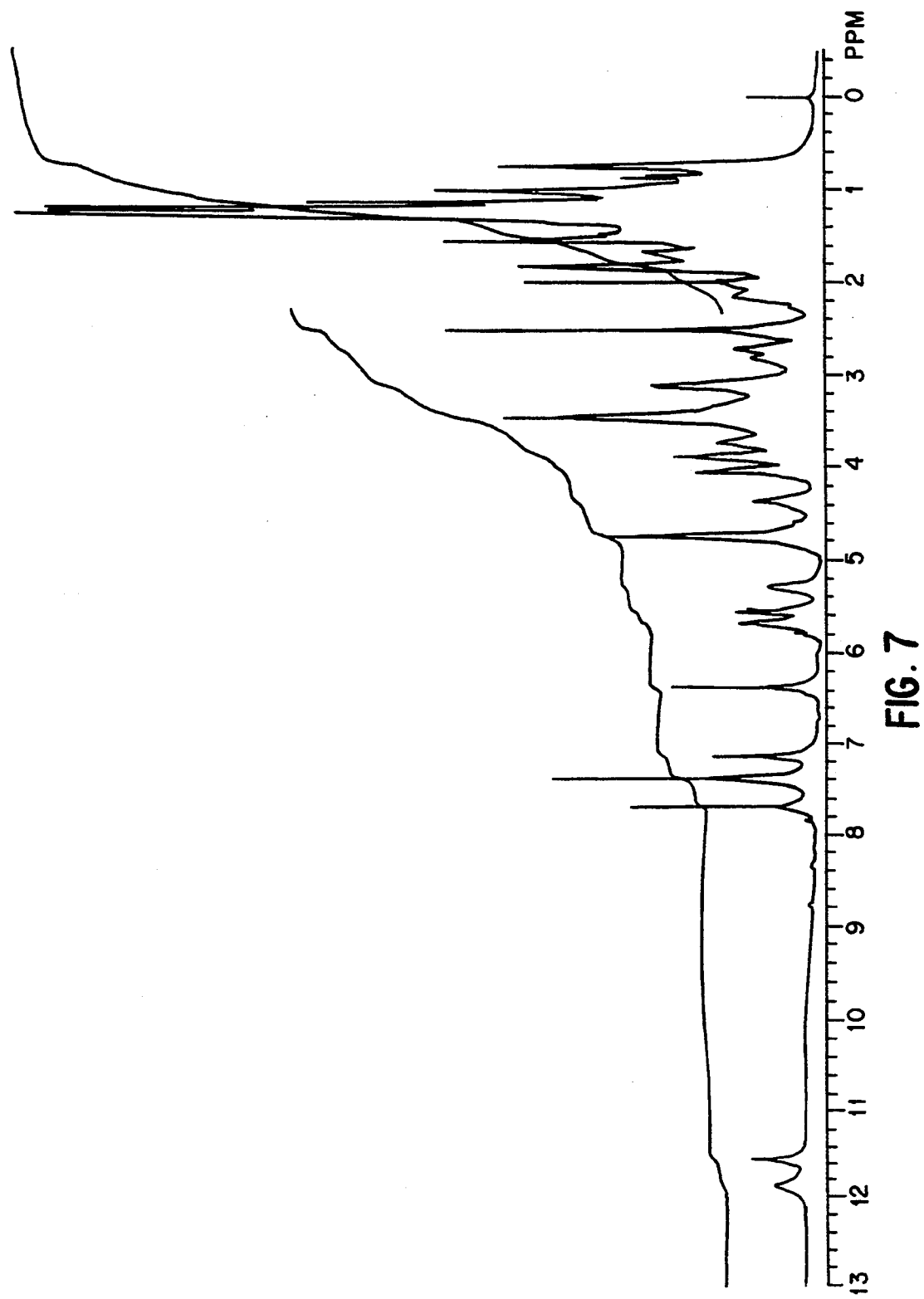
FIG. 7 shows a proton magnetic resonance spectrum of 42D005β.
Figure 8:
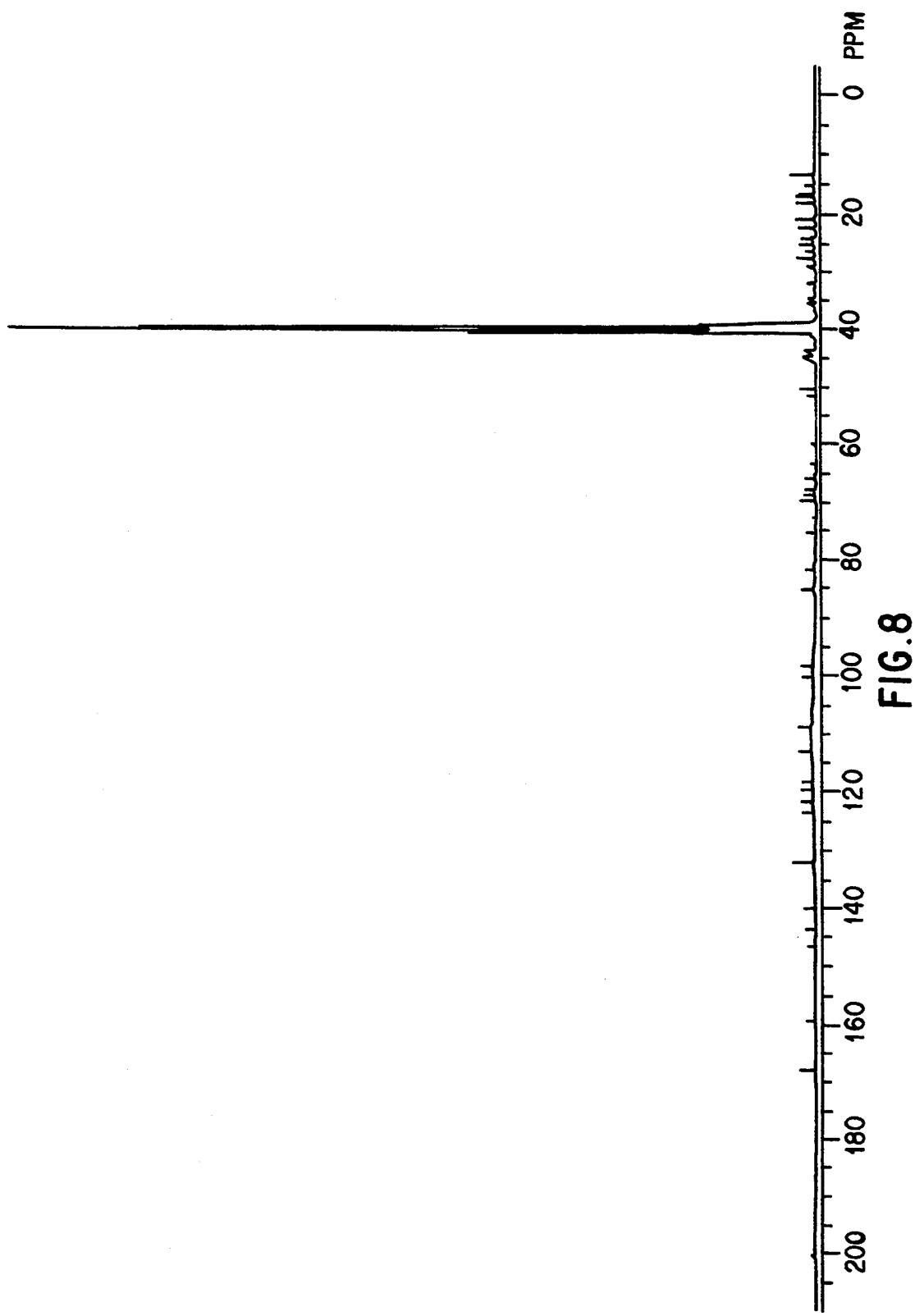
FIG. 8 shows a carbon-13 nuclear magnetic resonance spectrum of 42D005β.

1. Molecular weight: 1130;
   cal: 1153.5123 (M+Na+) high resolution mass spectrum;
2. Apparent molecular formula: $C_{60}H_{79}N_4O_{15}Cl$;
3. Specific rotation: $[\alpha]_D^{25} = -50 \pm 4$ (0.2% DMSO);
4. Ultraviolet absorption spectrum: as shown in FIG. 5 10 μg/ml in methanol
   229nm (ξ,26,100), 281nm (ξ,23,200), 335nm (ξ,25,600);
5. Infrared absorption spectrum as shown in FIG. 6: ($cm^{-1}$) 3426, 2972, 2933, 2878, 1684, 1626, 1598, 1567, 1540, 1447, 1405, 1383, 1295, 1270, 1236, 1204, 1163, 1092, 1032, 1017, 987, 971.
6. Proton nuclear magnetic resonance spectrum: as shown in FIG. 7:
   11.87(s,1H), 11.52(s,1H), 7.67(s,1H), 7.34(br.S,2H), 7.13 (d, 1H), 6.36 (s, 1H), 5.68 (m, 1H), 5.55 (d, 1H), 5.31 (m, 1H), 4.72 (m, 3H), 4.35 (br. s, 1H), 3.88 (m, 2H), 3.74 (m, 1H), 3.44 (m, 3H), 3.10 (m, 2H), 2.83 (m, 1H), 2.71 (m, 1H), 2.51 (m, 1H), 2.17 (m, 1H), 2.03 (m, 1H), 1.83 (m, 3H), 1.69 (m, 2H), 1.55 (m, 4H), 1.45 (m, 2H), 1.32(m,2H), 1.22(m,15H), 1.11(s,3H), 1.00(m,5H), 0.91(m,2H), 0.72(m,4H);
7. Carbon-13-nuclear magnetic resonance spectrum: as shown in FIG. 8 (DMSO), significant peaks as listed below:

| 200.1 | 121.6 | 84.9 | 50.2 | 31.5 | 16.9 |
| --- | --- | --- | --- | --- | --- |
| 200.0 | 121.1 | 81.7 | 45.1 | 28.9 | 16.6 |
| 170 | 119.6 | 80.0 | 44.9 | 27.7 | 14.8 |
| 167.8 | 118.2 | 75.1 | 44.6 | 27.5 | 13.2 |
| 159.2 | 112.9 | 69.6 | 44.3 | 26.1 | |
| 146.5 | 108.8 | 68.6 | 44.2 | 25.1 | |
| 143.3 | 108.7 | 67.9 | 43.9 | 24.5 | |
| 139.8 | 105.5 | 67.6 | 42.9 | 24.1 | |
| 131.9(2×) | 100.2 | 65.7 | 39.7 | 22.3 | |
| 123.3 | 100.0 | 63.0 | 35.2 | 20.8 | |
| 121.8 | 98.5 | 51.1 | 34.4 | 18.1 | |

2× = two overlapping signals

The new antibacterial agents 42D005α and 42D005β are formed during the cultivation under controlled conditions of a new strain of Kitasatosporia sp.

This microorganism is maintained in the culture collection of the Medical Research Division, American Cyanamid Company, Pearl River, N.Y. 10965 as culture number 42D005. A viable culture of this new microorganism has been deposited under the conditions of the Budapest Treaty with the Patent Culture Collection Laboratory, Northern Regional Research Center, U.S. Department of Agriculture, Peoria, Ill. 61604, and has been added to its permanent collection. It has been assigned the strain designation NRRL 21084 by said depository.

Culture 42D005 is isolated from a soil sample taken from Venice, Fla.

Culture 42D005 has the following cultural characteristics as described in Table I.

TABLE I

| CULTURAL CHARACTERISTICS | |
| --- | --- |
| Characteristic | 42D005 |
| Aerial Mycelium | Long Spore Chains |
| Fragmentation of Substrate Mycelium | None |
| Zoospores and Sporangia | None |
| Spore Chain | 8–15 |
| Spore Shape | Round |
| Spore Surface | Knobby |
| Temperature Growth | 22–45° C. |
| Salt Tolerance | <5% |
| DAP Analysis | 4:1 (meso:LL-DAP) |
| Whole Cell Sugars | Ribose, Mannose, Madurose, Galactose |

The macromorphology for culture 42D005 is described in Table II.

TABLE II

| MACROMORPHOLOGY | |
| --- | --- |
| Medium | 42D005 Morphology[a] |
| Yeast-Malt (ISP2) | G: Abundant<br>AM: White (263)<br>SM: Brown-Orange (54)<br>SP: None |
| Oatmeal (ISP3) | G: Abundant<br>AM: White (263)<br>SM: Pink-Yellow (89)<br>SP: None |
| Inorganic Salts-Starch (ISP4) | G: Abundant<br>AM: White (263)<br>SM: Bright Pink (33)<br>SP: None |
| Glycerol-Asparagine (ISP5) | G: Moderate<br>AM: White (263)<br>SM: Colorless<br>SP: None |

G, growth; AM, aerial mycelium; SM, substrate mycelium; SP, soluble pigment
[a]ISCC, National Bureau of Standard Centroid Color Charts, Publication 440, Washington, D.C., 1976.

The physiological reactions of 42D005 are shown in Table III.

TABLE III

| PHYSIOLOGICAL REACTIONS OF 42D005 | |
| --- | --- |
| Utilization of Carbon Sources: | |
| D-Glucose | + |
| L-Arabinose | + |
| Sucrose | − |
| D-Xylose | + |
| I-Inositol | ± |
| D-Mannitol | + |
| β-D-Fructose | + |
| a-L-Rhamnose | + |
| Raffinose | − |
| Cellulose | − |
| Hydrolysis of: | |
| Casein | + |
| Xanthine | − |
| Hypoxanthine | + |
| Tyrosine | − |
| Adenine | ± |

TABLE III-continued
PHYSIOLOGICAL REACTIONS OF 42D005

| | |
|---|---|
| Esculin | + |
| Production of: | |
| Urease | − |
| Melanin | − |
| Decarboxylation of: | |
| Acetate | + |
| Benzoate | − |
| Citrate | − |
| Lactate | + |
| Malate | + |
| Mucate | − |
| Oxalate | − |
| Proprionate | − |
| Pyruvate | + |
| Succinate | + |
| Tartrate | − |
| Acid Production from: | |
| Arabinose | + |
| Dulcitol | − |
| Erythritol | − |
| Glucose | + |
| Inositol | − |
| Lactose | − |
| Mannitol | + |
| Mannose | + |
| Methyl-a-D-glucoside | − |
| Melibiose | − |
| Raffinose | − |
| a-L-Rhamnose | + |
| Sorbitol | + |
| Trehalose | + |

+: positive, −: negative, ±: weak

It is to be understood that for the production of these new antibacterial agents the present invention is not limited to this particular organism or to organisms fully answering the above characteristics which are given for illustrative purposes only. In fact, it is desired and intended to include the use of mutants produced from this organism by various means such as exposure to X-radiation, ultraviolet radiation, N'-methyl-N'-nitro-N-nitrosoguanidine, actinophages and the like.

The in vitro antibacterial activity of 42D005α and β is determined against a spectrum of gram-positive and gram-negative bacteria by a standard agar dilution method. Mueller-Hinton agar with and without 5% sheep blood and two-fold decreasing concentrations of either 42D005α or β are poured into petri dishes. The agar surfaces are inoculated with 1 to $5 \times 10^4$ colony forming units of bacteria by means of the Steers replicating device. The lowest concentration of antibiotic that inhibits growth of a bacterial strain after 18 hours incubation is recorded as the minimal inhibitory concentration for that strain. The anti-bacterial activity results are given in Table IV and VI. The antibacterial activity results are given in Table V and VII with sheeps blood added to the agar.

TABLE IV
In vitro Antibacterial Activity of 42D005α

| Organism | Minimum Inhibitory Concentration mcg/ml 42D005α |
|---|---|
| 1. Staphylococcus aureus (MEMC-89-4) | 0.06 |
| 2. Staphylococcus aureus (ID-2371) | 0.06 |
| 3. Staphylococcus aureus (ID-3107) | 0.12 |
| 4. Staphylococcus aureus (ID-2727) | 0.06 |
| 5. Staphylococcus aureus (SMITH) | 0.12 |
| 6. Staphylococcus aureus (ID-3105) | 0.12 |
| 7. Staphylococcus aureus (ID-4379) | 0.12 |
| 8. Staphylococcus aureus (ATCC 29213)(Control Organism) | 0.06 |
| 9. Staphylococcus haemolyticus (ID-4061) | 0.06 |
| 10. CNS (ID-3135) | 0.06 |
| 11. CNS (ID-3276) | 0.12 |
| 12. CNS (ID-3120) | 0.06 |
| 13. CNS (ID-3941) | 0.12 |
| 14. CNS (ID-4615) | 0.06 |
| 15. E. faecalis (ID-4168) | 0.50 |
| 16. E. faecalis (ID-1829) | 0.50 |
| 17. E. faecalis (ID-2131) | 0.25 |
| 18. E. faecalis (ID-5353) | 0.5 |
| 19. E. faecalis (12201) | 0.25 |
| 20. E. faecalis (ATCC 29212) (Control Organism) | 0.50 |
| 21. E. faecium (12202) | 0.5 |
| 22. E. faecium (ID-251) | 0.5 |
| 23. E. faecium (ID-3301) | 0.25 |
| 24. E. faecalis (ID-4133) | 0.25 |
| 25. E. avium (ID-3953) | 0.25 |
| 26. P. aeruginosa ATCC 27853 | >64 |
| 27. M. morganii VGH 84-11 (in vitro model) | >64 |
| 28. E. coli J2175 (Parent of 2445) | >64 |
| 29. E. coli (J2445) (IMP mutant) | 1 |
| 30. E. coli ATCC 25922 | >64 |
| 31. B. cereus (Bacto) (Assay Organism) | 0.06 |
| 32. S. lutea ATCC 9341 | 0.03 |

TABLE V
In vitro Antibacterial Activity of 42D005α
In the Presence of Sheeps Blood*

| Organism | Minimum Inhibitory Concentration mcg/ml 42D005α |
|---|---|
| 1. Staphylococcus aureus (MEMC-89-4) | 2 |
| 2. Staphylococcus aureus (ID-2371) | 8 |
| 3. Staphylococcus aureus (ID-3107) | 8 |
| 4. Staphylococcus aureus (ID-2727) | 4 |
| 5. Staphylococcus aureus (SMITH) | 8 |
| 6. Staphylococcus aureus (ID-3105) | 8 |
| 7. Staphylococcus aureus (ID-4379) | 8 |
| 8. Staphylococcus aureus (ATCC 29213) (Control Organism) | 2 |
| 9. Staphylococcus haemolyticus (ID-4061) | 2 |
| 10. CNS (ID-3135) | 2 |
| 11. CNS (ID-3276) | 2 |
| 12. CNS (ID-3120) | 1 |
| 13. CNS (ID-3941) | 2 |
| 14. CNS (ID-4615) | 2 |
| 15. E. faecalis (ID-4168) | 16 |
| 16. E. faecalis (ID-1829) | 16 |
| 17. E. faecalis (ID-2131) | 8 |
| 18. E. faecalis (ID-5353) | 16 |
| 19. E. faecalis (12201) | 8 |
| 20. E. faecalis (ATCC 29212) (Control Organism) | 16 |

TABLE V-continued

In vitro Antibacterial Activity of
42D005α
In the Presence of Sheeps Blood*

| Organism | Minimum Inhibitory Concentration mcg/ml 42D005α |
|---|---|
| 21. E. faecium (12202) | 16 |
| 22. E. faecium (ID-251) | 8 |
| 23. E. faecium (ID-3301) | 16 |
| 24. E. faecalis (ID-4133) | 8 |
| 25. E. avium (ID-3953) | 16 |
| 26. P. aeruginosa ATCC 27853 | >16 |
| 27. M. morganii VGH 84-11 (in vitro model) | >16 |
| 28. E. coli J2175 (Parent of 2445) | >16 |
| 29. E. coli (J2445) (IMP mutant) | |
| 30. E. coli ATCC 25922 | >16 |
| 31. B. cereus (Bacto) (Assay Organism) | 8 |
| 32. S. lutea ATCC 9341 | 0.25 |

*The pH is adjusted to between 7 and 8 with sodium hydroxide.

TABLE VI

In vitro Antibacterial Activity of
42D005β

| Organism | Minimum Inhibitory Concentration mcg/ml 42D005β |
|---|---|
| 1. Staphylococcus aureus (MEMC-89-4) | 0.25 |
| 2. Staphylococcus aureus (Rose) | 0.12 |
| 3. Staphylococcus aureus (IVES 6-542) | 0.12 |
| 4. Staphylococcus aureus (IVES 5-160) | 0.03 |
| 5. Staphylococcus aureus (IVES 5-396) | 0.25 |
| 6. Staphylococcus aureus (310:MRSA) | 0.12 |
| 7. Staphylococcus aureus (K82-26) | 0.25 |
| 8. Staphylococcus aureus (CMC-83-131) | 0.06 |
| 9. Staphylococcus Smith | 0.5 |
| 10. Staphylococcus aureus ATCC 29213 | 0.06 |
| 11. Staphylococcus aureus ATCC 25923 | 0.5 |
| 12. S. hemolyticus ID-4061 | 0.25 |
| 13. S. hemolyticus AVAH-88-3 | 0.25 |
| 14. S. epi IVES 2-455 | 0.12 |
| 15. S. epi ATCC 12228 | 0.25 |
| 16. E. faecalis (ARUM-87-41) | 0.50 |
| 17. E. faecalis (CHBM 88-60) | 0.5 |
| 18. Enterococcus (379 VancoR.) | 0.5 |
| 19. E. faecalis (UCI 85-30) | 0.5 |
| 20. E. faecalis (VGH 84-69) | 0.5 |
| 21. E. faecalis (CMC 83-120) | 0.5 |
| 22. Streptococcus (GroAAMCH) 8884 | 2 |
| 23. Streptococcus (GrpBAMCH) 88-86 | 0.06 |
| 24. Streptococcus pneumo. (CHBM 88-25) | 0.05 |
| 25. Streptococcus pneumo. (TEX 852) | 0.5 |
| 26. Streptococcus pneumo. (CHBM 88-70) | 0.5 |
| 27. K. pneumo. NEMC 82-271 | >64 |
| 28. E. coli (ID-9003) | >64 |
| 29. E. coli ID-5043 | 1 |
| 30. E. coli (ATCC 25922) | >64 |
| 31. E. coli ATCC 35218 | >64 |
| 32. B. cereus (Davies) | 0.5 |

TABLE VII

In vitro Antibacterial Activity of
42D005β
In the Presence of 5% Sheeps Blood

| Organism | Minimum Inhibitory Concentration mcg/ml 42D005β |
|---|---|
| 1. Staphylococcus aureus (MEMC-89-4) | 16 |
| 2. Staphylococcus aureus (Rose) | 16 |
| 3. Staphylococcus aureus (IVES 6-542) | |
| 4. Staphylococcus aureus (IVES 5-160) | 4 |
| 5. Staphylococcus aureus (IVES 5-396) | 16 |
| 6. Staphylococcus aureus (310:MRSA) | 16 |
| 7. Staphylococcus aureus (K82-26) | 32 |
| 8. Staphylococcus aureus (CMC-83-131) | 4 |
| 9. Staphylococcus Smith | 16 |
| 10. Staphylococcus aureus ATCC 29213 | 4 |
| 11. Staphylococcus aureus ATCC 25923 | 16 |
| 12. S. hemolyticus ID-4061 | 16 |
| 13. S. hemolyticus AVAH-88-3 | 16 |
| 14. S. epi IVES 2-455 | 4 |
| 15. S. epi ATCC 12228 | 4 |
| 16. E. faecalis (ARUM-87-41) | 32 |
| 17. E. faecalis (CHBM 88-60) | 16 |
| 18. Enterococcus (379 VancoR.) | 32 |
| 19. E. faecalis (UCI 85-30) | 16 |
| 20. E. faecalis (VGH 84-69) | 16 |
| 21. E. faecalis (CMC 83-120) | 16 |
| 22. Streptococcus (GroAAMCH) 8884 | 32 |
| 23. Streptococcus (GrpBAMCH) 88-86 | 16 |
| 24. Streptococcus pneumo. (CHBM 88-25) | 16 |
| 25. Streptococcus pneumo. (TEX 852) | 16 |
| 26. Streptococcus pneumo. (CHBM 88-70) | 16 |
| 27. K. pneumo. NEMC 82-271 | >64 |
| 28. E. coli (ID-9003) | >64 |
| 29. E. coli ID-5043 | 32 |
| 30. E. coli (ATCC 25922) | >64 |
| 31. E. coli ATCC 35218 | >64 |
| 32. B. cereus (Davies) | 16 |

The antibacterial results show that the products according to the invention have a broad spectrum of activity against the bacterial strains tested.

The products according to the invention which have good antimicrobial activity, can be used in antimicrobial compositions for general antibacterial uses especially as antiseptics by local and general application, and as disinfectants.

As antiseptics for human or veterinary use, the concentration of active product can vary from 0.01% to 5% by weight according to the use and the chosen formulation. Thus, it is possible to prepare foaming detergent solutions to be used by surgeons and nursing staff for washing their hands or to be used for cleansing dermatological lesions such as impetigo, pityriasis and leg ulcers. Foaming detergent solutions are also used as shampoos (for example antidandruff shampoos) or for the preparation of shower gels, shaving creams and foaming lotions. Foaming solutions containing products according to the invention are obtained using amphoteric, anionic, cationic or non-ionic surfactants at a concentration of 0.3 to 30%, humectants, such as glycols or polyethylene glycols, at a concentration of 0 to 20%, ethylene oxide and polypropylene copolymers at a concentration of 0 to 20%, and an alcohol (ethanol, isopropanol, benzyl alcohol) or a polyol, such as glycerol, at a concentration of 0 to 15%, as well as agents for complexing Ca++, Mg++ and heavy metal ions, salts for providing an appropriate buffer capacity, agents for imparting viscosity, such as NaCl or KCl, natural, cellulosic or synthetic polymers such as polyvinylpyrrolidone, thickening superfatting agents such as polyethylene glycol distearate or copra mono-ethanolamide or diethanolamide, fragrances, preservatives and colorants.

If the product according to the invention has a poor solubility in water, it is possible to use microemulsions, micellar solutions or any other phase of the ternary or quaternary diagram of water/active principle/surfactant/co-surfactant which permits solubilization in water. These solutions can be used in diluted or undiluted form and can be dispensed for example by means of a vasopump or liquefied or non-liquefied propellants.

With the same constituents at appropriate concentrations, the products according to the invention can also be used to prepare simple aqueous solutions or aqueous solutions in the form of sprays for making operative fields antiseptic, for postoperative treatments, for the treatment of burns, superinfected eczema, gluteal erythema, wounds or ache, or for deodorants.

Simple alcoholic solutions or alcoholic solutions in the form of sprays containing 20 to 80% by weight of alcohol can contain, apart from the excipients used in aqueous solutions, excipients which make it possible to penetrate the keratinized layers of the skin and superficial body growths, such as Azone (marketed by Nelson Research) and Transcutol (marketed by Gattefosse). These solutions are to be used for making the skin antiseptic before puncture, for preparing the operative field, by nursing staff for making their hands antiseptic and for treating closed infected dermatosis, folliculitis, perionychia or acne.

The products according to the invention can be applied in the form of creams which contain some of the compounds mentioned for the preparation of solutions, together with the fatty substances normally found in the preparation of creams or emulsions. These creams can be used especially for the prevention of superinfections of gluteal erythema, eczema, mycosis or acne.

The products according to the invention can also be used for the treatment or prevention of sexually transmitted diseases in the form of gynecological sponges or washes.

The products according to the invention can be administered in the form of sprays or solutions. In addition, the solutions or sprays can be used to rinse contact lenses.

The products according to the invention can also be used in animals for indications such as the prevention or treatment of infected lesions liable to become superinfected. In this case, the pharmaceutical compositions are similar to those used in man, in particular creams, sprays or solutions.

Moreover, the rapid lethal action on germs of the products according to the invention enables them to be used as surface disinfectants at concentrations which can vary from 0.1 to 4% by weight. In this case, the products are used in preparations such as aqueous or non-aqueous foaming detergent solutions, sprays or nebulizers. Preparations of this type are particularly useful in the hospital or veterinary sectors, for local communities or agrifoodstuff industries. These preparations can contain the same constituents as those used in the antiseptic formulations, although a variety of organic solvents may be added.

In therapeutic use, the compounds of this invention may be administered in the form of conventional antimicrobial pharmaceutical compositions appropriate for the intended use.

In therapeutic use, the compounds of this invention may be administered in the form of conventional pharmaceutical compositions appropriate for the intended use.

GENERAL FERMENTATION CONDITIONS

Cultivation of Kitasatosporia sp. 42D005 may be carried out in a wide variety of liquid culture media. Media which are useful for the production of 42D005 include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

GENERAL PROCEDURE FOR THE ISOLATION OF 42D005α AND 42D005β

The 42D005α and 42D005β are recovered from the fermentation broth at pH 5.0–6.0, filtration through diatomaceous earth, extraction into a solvent such as ethyl acetate, filtering through a ceramic membrane filter, washing the filter with ethyl acetate followed by water and concentrating the ethyl acetate phase giving a crude product.

The crude product is then separated into the α and β components and further purified by high performance liquid chromatography on a reverse-phase column using the system 40% acetonitrile: 0.4% tetrafluoroacetic acid followed by methanol-acetonitrile (3:1).

The invention will be further described in conjunction with the following non-limiting examples.

EXAMPLE 1

Inoculum Preparation

A typical medium used to grow the primary inoculum is prepared according to the following formula:

| | |
|---|---|
| Glucose | 1.0% |
| Dextrin | 2.0% |
| Yeast extract | 0.5% |
| NZ Amine A ®[1] | 0.5% |
| Mississippi line | 0.1% |
| FD-82 defoamer | 0.3% |
| Water qs | 100.0% |

[1][A pancreatic digest of casein, registered trademark of Sheffield Chemical, Norwich, NY]

This medium is sterilized and 100 ml, in a 500 ml flask, is inoculated with Kitasatosporia sp. The medium is then placed on a rotary shaker and incubated at 28° C. for 48 hours providing a primary inoculum. This primary inoculum is then used to inoculate 10 liters of the same sterile medium in a bottle. This medium is grown at 28° C. for 48 hours with a sterile air flow of 200 liters per liter of mash per minute and agitation by an impeller driven at 500 rpm, providing a tertiary inoculum.

EXAMPLE 2

Fermentation

A fermentation medium of the following formulation is prepared:

| | |
|---|---|
| Bacto-peptone | 1.0% |
| Glucose | 1.0% |
| Molasses | 2.0% |
| Calcium carbonate | 0.1% |
| FD-82 antifoam | 0.3% |
| Ferric ammonium citrate | 0.01% |
| Water qs | 100.0% |

This medium is sterilized and 1500 liters is then inoculated with 150 liters of tertiary inoculum from Example 1. The fermentation is conducted at 28° C. with a sterile air flow of 1250 liters per minute and agitation by an impeller driven at 110 rpm for 75 hours, at which time the mash is harvested.

EXAMPLE 3

Isolation and Purification of 42D005α and β

The mash from two fermentations, one conducted as described in Example 2 and the second as described in Example 2 on a 300 liter scale are combined and mixed with 16.5 liters of toluene. A 1300 liter volume of ethyl acetate is added and mixed or two hours. The pH is 5.5. The broth is filtered through a 0.2 micron ceramic membrane filter. The retentate is washed with 100 liters of ethyl acetate followed by 100 liters of water. After separation, the pH of the ethyl acetate phase is adjusted to 9–10 with concentrated ammonium hydroxide. The ethyl acetate phase is concentrated to 30 liters. The pH is maintained at 9 by adding 20 ml of concentrated ammonium hydroxide. Further concentration brings the volume to 1–2 liters.

The residual ethyl acetate is removed under reduced pressure and the crude extract is dissolved in 1 liter of methyl alcohol. The methyl alcohol is washed three times with hexanes to remove antifoaming agent additives. The methyl alcohol solution is concentrated to 500 ml.

The crude product is purified by chromatography in separate 50 ml portions by mixing with water until cloudy and is injected onto a reverse-phase column $C_{18}$ (protein and peptide, 55×250 mm guard column) equilibrated with 50% acetonitrile in 0.4% tetrafluoroacetic acid water solution at a flow rate 40 ml/minute; detected at 280/330 nm double wavelength. The products 42D005α and 42D005β eluted in about 80 minutes and 100 minutes, respectively, in a gradient system ($CH_3CN$:50%:40 minutes; 51.2%:25 minutes; 52.5%:45 minutes; 55%; 15 minutes; 85%:25 minutes with 40 ml/minute flow rate). About one equal volume of water is added to the pooled fractions separately for α and β, and the resulting solution is pumped through a reverse-phase column ($C_{18}$ bonded phase 40 micron) at a flow rate of 20 ml/minute. The column is washed with distilled water at a flow rate of 10 ml/minute or 5 minutes, followed by 20 ml of 3:1 methyl alcohol/acetonitrile at a flow rate of 10 ml/minute. Pooled fractions from each of separate purifications is concentrated to dryness to give 400 mg of 42D005α and 2.85 g of 42D005β as solid.

What is claimed is:

1. The compound 42D005α which has the structure:

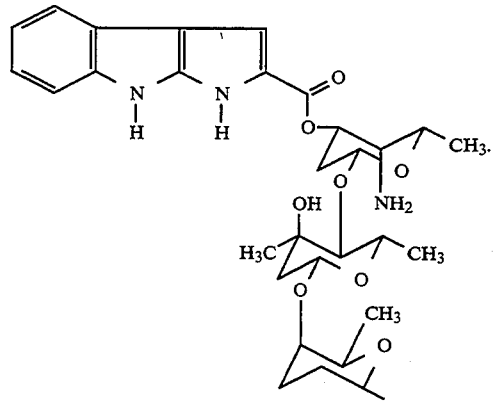

2. The compound 42D005β which has the structure:

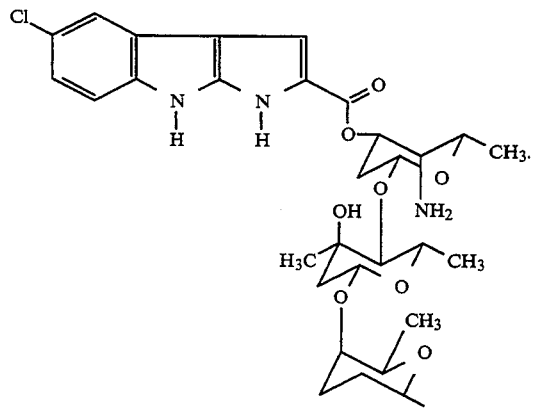

-continued

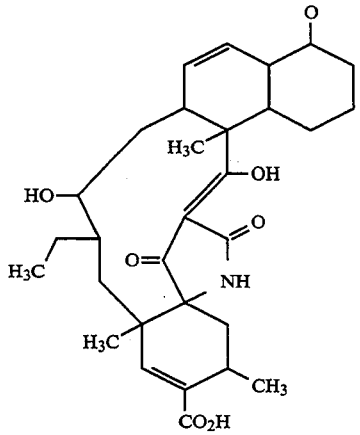

3. A pharmaceutical, disinfectant, or cosmetic composition which contains an effective anti-microbial, disinfectant or preservative amount of the 42D005α compound of claim 1 as an active ingredient.

4. A pharmaceutical, disinfectant, or cosmetic composition which contains an effective anti-microbial, disinfectant or preservative amount of the 42D005β compound of claim 2 as an active ingredient.

5. A pharmaceutical composition having antimicrobial and disinfectant activity as claimed in claim 3 wherein said effective amount of said antimicrobial compound 42D005α is from 0.01 to 5% by weight.

6. A pharmaceutical composition having antimicrobial and disinfectant activity as claimed in claim 4 wherein said effective amount of said antimicrobial compound 42D005β is from 0.01 to 5% by weight.

7. A disinfectant composition for inert surfaces as claimed in claim 3, wherein said effective amount of said antimicrobial compound 42D005α is from 0.1 to 4% by weight.

8. A disinfectant composition for inert surfaces as claimed in claim 4 wherein said effective amount of said antimicrobial compound 42D005α is from 0.1 to 4% by weight.

9. A pharmaceutical composition as claimed in claim 3, wherein said effective amount of said antimicrobial compound 42D005α is from 0.005 to 0.5% by weight.

10. A pharmaceutical composition as claimed in claim 4, wherein said effective amount of said antimicrobial compound 42D005β is from 0.005 to 0.5% by weight.

11. A cosmetic composition as claimed in claim 3 wherein said effective amount of said antimicrobial compound 42D005α is from 0.01 to 5% by weight.

12. A cosmetic composition as claimed in claim 4 wherein said effective amount of said antimicrobial compound 42D005α is from 0.01 to 5% by weight.

* * * * *